United States Patent
Yamauchi

(10) Patent No.: US 7,472,578 B2
(45) Date of Patent: Jan. 6, 2009

(54) GAS SENSOR

(75) Inventor: Masanobu Yamauchi, Kariya (JP)

(73) Assignee: Denso Corporation (JP)

( * ) Notice: Subject to any disclaimer, the term of this patent is extended or adjusted under 35 U.S.C. 154(b) by 71 days.

(21) Appl. No.: 11/594,816

(22) Filed: Nov. 9, 2006

(65) Prior Publication Data

US 2007/0113617 A1  May 24, 2007

(30) Foreign Application Priority Data

Nov. 10, 2005  (JP) ............................ 2005-326464
Jul. 13, 2006   (JP) ............................ 2006-192590

(51) Int. Cl.
*G01M 15/00* (2006.01)
*G01N 27/407* (2006.01)

(52) U.S. Cl. ...................... 73/23.31; 73/31.05; 204/424

(58) Field of Classification Search ................ 73/23.31, 73/23.32, 31.05; 204/424, 425, 426, 427, 204/428, 429

See application file for complete search history.

(56) References Cited

U.S. PATENT DOCUMENTS 4,209,377 A * 6/1980 Shinohara et al. ............ 204/424
6,615,641 B2 * 9/2003 Kojima ....................... 73/23.31
6,878,252 B2 * 4/2005 Weyl et al. .................... 204/424
2003/0024300 A1 * 2/2003 Kojima ........................ 73/31.05
2006/0213254 A1 * 9/2006 Satou et al. .................. 73/31.05

FOREIGN PATENT DOCUMENTS

JP    2003-294684    10/2003

* cited by examiner

*Primary Examiner*—Michael Cygan
(74) *Attorney, Agent, or Firm*—Nixon & Vanderhye PC

(57) ABSTRACT

A gas sensor is disclosed having an element holder body with which a sensor element is fixedly supported, and an atmosphere-side insulator covering a base portion of the sensor element and providing electrical connection between lead wires and terminal electrodes of the sensor element. The element holder body includes a housing and an element-side insulator fixedly mounted in the housing. The atmosphere-side insulator incorporates therein a plurality of spring terminals held in electrical contact with the electrode terminals of the sensor element. At least one of the element holder body and the atmosphere-side insulator carries thereon convexed portions with which the atmosphere-side insulator can tilt with respect to the element holder body.

9 Claims, 16 Drawing Sheets

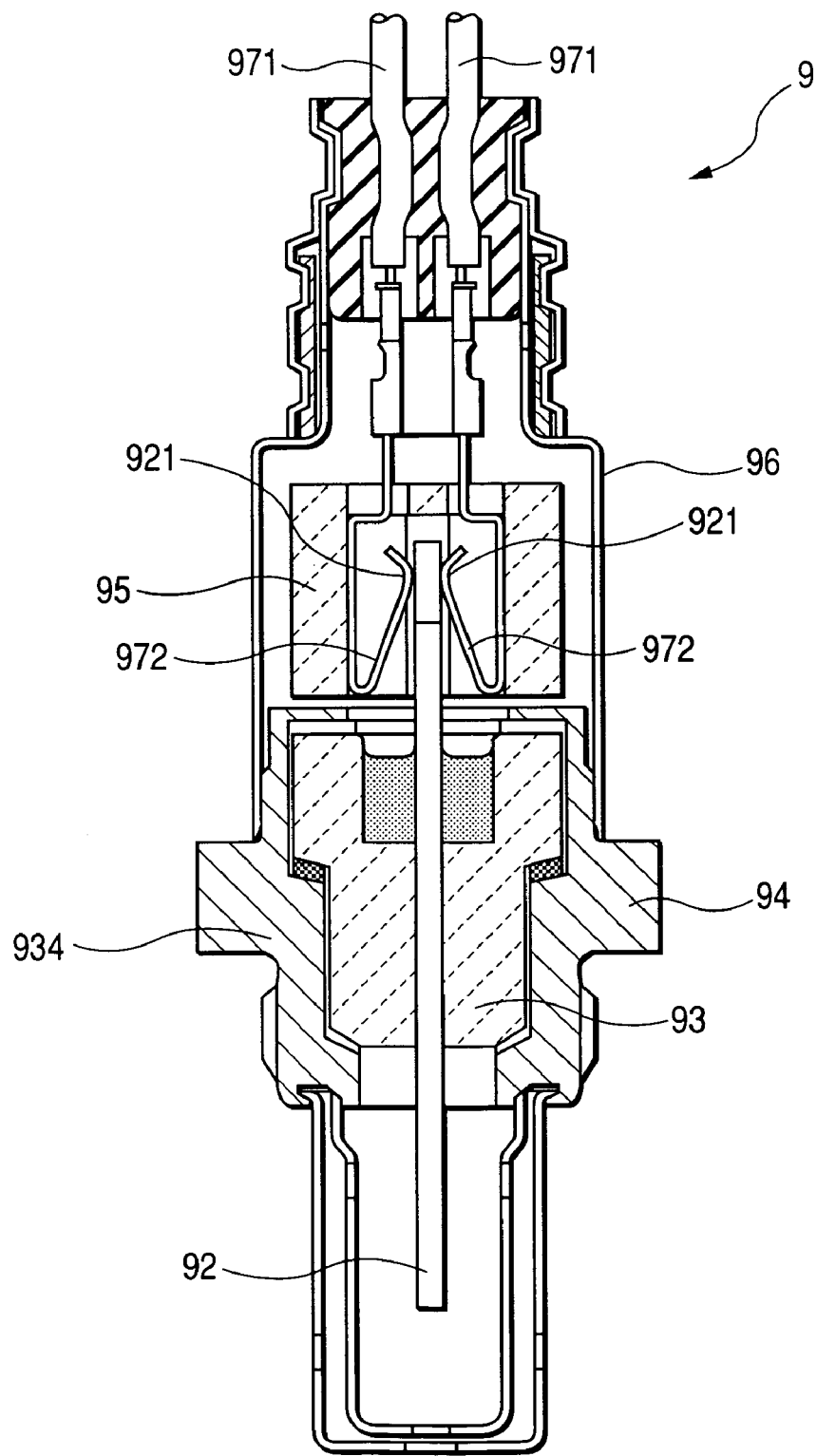

GAS SENSOR

CROSS REFERENCE TO RELATED APPLICATIONS

This application is related to Japanese Patent Application No. 2005-326464 and No. 2006-192590, filed on Nov. 10, 2005 and Jul. 13, 2006, respectively, the contents of which are hereby incorporated by reference.

BACKGROUND OF THE INVENTION

1. Technical Field of the Invention

The present invention relates to a gas sensor for detecting a concentration of specified gas in gas to be measured.

2. Description of the Related Art

In related art, it has been a common practice for an internal combustion engine of a motor vehicle to have an exhaust system on which a gas sensor is mounted for measuring a concentration of specified gas such as oxygen or nitrogen oxide contained in exhaust gases.

One example of such a gas sensor is disclosed in Japanese Unexamined Patent Publication No. 2003-294684. Such a related art gas sensor is shown in FIGS. 14 to 17. As shown in FIG. 14, a gas sensor 9 comprises a sensor element 92, composed of a plate-like bar, which has a detecting section for detecting a concentration of specified gas in measuring gas, which is inserted to and supported with an element-side insulator 93. The element-side insulator 93 is disposed in and supported with a housing 94. The sensor element 92 has an upper base end that is covered with an atmosphere-side insulator 95 placed in axial alignment with the element-side insulator 93. Further, the housing 94 has a base end that fixedly supports an atmosphere-side cover 96 with which the atmosphere-side insulator 95 is covered.

The upper base end of the sensor element 92 has opposing surfaces formed with electrode terminals 921 electrically connected to the detecting section. The atmosphere-side insulator 95 internally accommodates a plurality of spring terminals 972 held in electrical contact with the electrode terminals 921 of the sensor element 92 to provide electrical connection between the electrode terminals 921 and lead wires 971. With such a structure, mounting the atmosphere-side insulator 95 on the base end portion of the sensor element 92 so as to cover the same allows the spring terminals 972 to be brought into pressured contact with the electrode terminals 921 of the sensor element 92.

With the structure set forth above, the sensor element 92 is apt to be held with an element holder 934, composed of the housing 94 and the element side insulator 93, under a tilted condition with respect to an axial direction of the element holder 934. Under such a situation, as shown in FIG. 15, if an attempt is made to locate the atmosphere-side insulator 95 on an upper surface of the element holder 934 with an end face 951 of the atmosphere-side insulator 95 held in contact with a base end face 935 of the element holder 934, a deterioration occurs in a positional relationship between the spring terminals 972, accommodated in an inside of the atmosphere-side insulator 95, and the electrode terminals 921 of the sensor element 92. This results in defective electrical contact between the spring terminals 972 and the electrode terminals 921 of the sensor element 92.

Further, with a requirement for the sensor element 92 to be miniaturized in structure, the sensor element 92 needs to have a narrowed width. With such a structure of the sensor element 92, the electrode terminals 921 also need to have extremely narrowed widths. Thus, the narrower the widths of the electrode terminals 921 formed on the sensor element 92, the more frequent will be for the occurrence of defective electrical contact between the spring terminals 972 and the electrode terminals 921 of the sensor element 92.

With a view to addressing such an issue, it is conceivable for the atmosphere-side insulator 95 to be formed with an inner wall 95a decreased in diameter providing a narrowed clearance 95b between the inner bore 95a of the atmosphere-side insulator 95 and an outer periphery of the sensor element 92 as shown in FIG. 16. With such a structure, however, if the atmosphere-side insulator 95 is placed in a position with reference to the upper end face of the element holder 934 with the sensor element 92 supported in a condition tilted to the element holder 934, a risk liable to occur between the base end of the sensor element 92 and the inner wall 95a of the atmosphere-side insulator 95. This results in a risk of causing damage to the sensor element 92.

With a view to avoiding such an issue, it is also conceivable for the atmosphere-side insulator 95 to be placed with reference to the sensor element 92 in place of the element holder 934 for ensuring correct electrical conductance between the electrode terminals 921 and the spring terminals 972 while avoiding the interference between the sensor element 92 and the atmosphere-side insulator 95 as shown in FIG. 17. With such a structure, an attempt is made to cause an axis of the sensor element 92 and an axis of the atmosphere-side insulator 95 to be aligned with each other even with the sensor element 92 fixed in a condition tilted to the element holder 934 under which the atmosphere-side insulator 95 remains floating from the element holder 934.

However, with the sensor element 92 fixed in the condition tilted to the element holder 934, the atmosphere-side insulator 95 becomes unstable in structure. Under such a circumstance, a risk occurs for a corner area 952 of the end face 951 of the atmosphere-side insulator 95 to conflict the element holder 934, causing damage to the electrode terminals 921 of the sensor element 92.

SUMMARY OF THE INVENTION

The present invention has been completed with a view to addressing the above issue and has an object to provide a gas sensor that can ensure a favorable electrical contact between electrode terminals of a sensor element and spring terminals of an atmosphere-side insulator while enabling the atmosphere-side insulator to be stably placed with respect to an element holder.

To achieve the above object, one aspect of the present invention provides a gas sensor comprising an element holder body including a housing, available to be mounted on a gas flow passage for gas to be measured, and an insulation member fixedly supported in the housing. A sensor element, fixedly supported in the insulation member, has a base end whose opposing surfaces are formed with a plurality of electrode terminals, respectively. An atmosphere-side insulator covers the base end of the sensor element and internally incorporating a plurality of spring terminals held in contact with the electrode terminals, respectively. A tilting device is disposed between the atmosphere-side insulator and the element holder body to allow the atmosphere-side insulator to tilt at a given tilting angle on a plane parallel to the surfaces of the sensor element.

With the gas sensor set forth above, the atmosphere-side insulator is disposed in an area closer to the element holder body so as to match with the sensor element in an axial direction. That is, the tilting device is disposed between the atmosphere-side insulator and the element holder body to allow the atmosphere-side insulator to be located with reference to the sensor element instead of the element holder body. With such configuration, even if the sensor element is tilted to the sensor element, no probability takes place for the spring terminals of the atmosphere-side insulator to be dislocated from the electrodes terminals of the sensor element, thereby ensuring electrical conductance between the spring terminals and the electrodes terminals in a highly reliable fashion.

With the gas sensor of the present embodiment, the tilting device may comprise convexed portions formed on a distal end of the atmosphere-side insulator along an axis parallel to a biasing direction of each of the spring terminals.

With the gas sensor of the present embodiment, further, the tilting device may comprise convexed portions formed on a base end of the element holder body along an axis parallel to a biasing direction of each of the spring terminals.

With such a structure, the atmosphere-side insulator is supported on the element holder body by means of the tilting device and can be placed in a stable position. Also, providing the tilting device enables the atmosphere-side insulator to be held in abutting engagement with the element holder body to be tiltable with respect thereto. Thus, the atmosphere-side insulator can be tilted at freely variable angles with respect to the element holder body. As a result, the atmosphere-side insulator can be tilted at a given angle depending on a degree of inclination of the sensor element.

With the gas sensor of the present embodiment, the element holder body may comprise an atmosphere-side cover fixedly secured to a base end of the housing so as to cover the atmosphere-side insulator, and an inner protection cylinder disposed inside the atmosphere-side cover and fixedly supported with the base end of the housing in an area outside the atmosphere-side insulator. The tilting device may comprise a radial protrusion, radially extending from the atmosphere-side insulator in an area inside the atmosphere-side cover, which is held in abutting engagement with the inner protection cylinder to be tiltable at the given tilting angle.

With the structure described above, the tilting device comprises the radial protrusion, radially extending from the atmosphere-side insulator inside the atmosphere-side cover, and the inner protection cylinder disposed inside the atmosphere-side cover, with the radial protrusion held in abutting engagement with the inner protection cylinder. Thus, even if the sensor element is tilted to the sensor element, the atmosphere-side insulator can be tilted at given angle while maintaining coaxial alignment between the sensor element and the atmosphere-side insulator. Thus, no probability takes place for the spring terminals of the atmosphere-side insulator to be dislocated from the electrodes terminals of the sensor element, thereby ensuring electrical conductance between the spring terminals and the electrodes terminals in a highly reliable fashion.

With the gas sensor of the present embodiment, the tilting mechanism may comprise a convexed portion formed on the radial protrusion of the atmosphere-side insulator.

With such a structure, the formation of the convexed portion on the radial protrusion of the atmosphere-side insulator causes no increase in component parts of the gas sensor, which can be simplified in structure with lightweight while achieving low cost.

With the gas sensor of the present embodiment, the tilting mechanism may comprise a convexed portion formed on the inner protection cylinder in abutting engagement with the radial protrusion of the atmosphere-side insulator.

With such a structure, the formation of the convexed portion on the inner protection cylinder causes no increase in component parts of the gas sensor, which can be simplified in structure with lightweight while achieving low cost.

With the gas sensor of the present embodiment, the tilting device may comprise a convexed portion formed on one of the atmosphere-side insulator and the element holder body has the relationship expressed as H/W>0.1 where H represents a protruding length of the convexed portion from one of the atmosphere-side insulator and the element holder body and W represents a smaller width of the one of the atmosphere-side insulator and the element holder body than a width of the other one of the atmosphere-side insulator and the element holder body.

Providing the convexed portion formed on one of the atmosphere-side insulator and the element holder body with the relationship expressed as H/W>0.1 enables the atmosphere-side insulator to be tilted to the element holder body at the given angle. Therefore, none of the spring terminals of the atmosphere-side insulator is dislocated from the electrodes terminals of the sensor element, thereby ensuring electrical conductance between the spring terminals and the electrodes terminals in a highly reliable fashion.

With the gas sensor of the present embodiment, the housing may include a holder body member, a first cylindrical extension, extending in a direction toward the atmosphere-side insulator and internally holding the insulation member, and a second cylindrical extension extending from the holder body member in opposition to the first cylindrical extension. The first cylindrical extension has a radially inward portion facing the atmosphere-side insulator, and the tilting member comprises a convexed portion held in abutting engagement with the radially inward portion of the first cylindrical extension.

The provision of the tilting member including the convexed portion held in abutting engagement with the radially inward portion of the first cylindrical extension enables the atmosphere-side insulator to be tilted to the element holder body with the utilization of the radially inward portion of the first cylindrical extension. Thus, none of the spring terminals carried by the atmosphere-side insulator is dislocated from the electrodes terminals of the sensor element, thereby ensuring electrical conductance between the spring terminals and the electrodes terminals in a highly reliable fashion. Also, such a structure causes no increase in component parts of the gas sensor, which can be simplified in structure with lightweight while achieving low cost.

With the gas sensor of the present embodiment, the insulation member may comprise an element-side insulator including a cylindrical body whose base end extends from the housing of the element holder body, and wherein the tilting device may comprise a convexed portion held in abutting engagement with the atmosphere-side insulator.

BRIEF DESCRIPTION OF THE DRAWINGS

FIG. 14 is a longitudinal sectional view of a gas sensor of the related art.

DETAILED DESCRIPTION OF PREFERRED EMBODIMENTS

Figure 1:
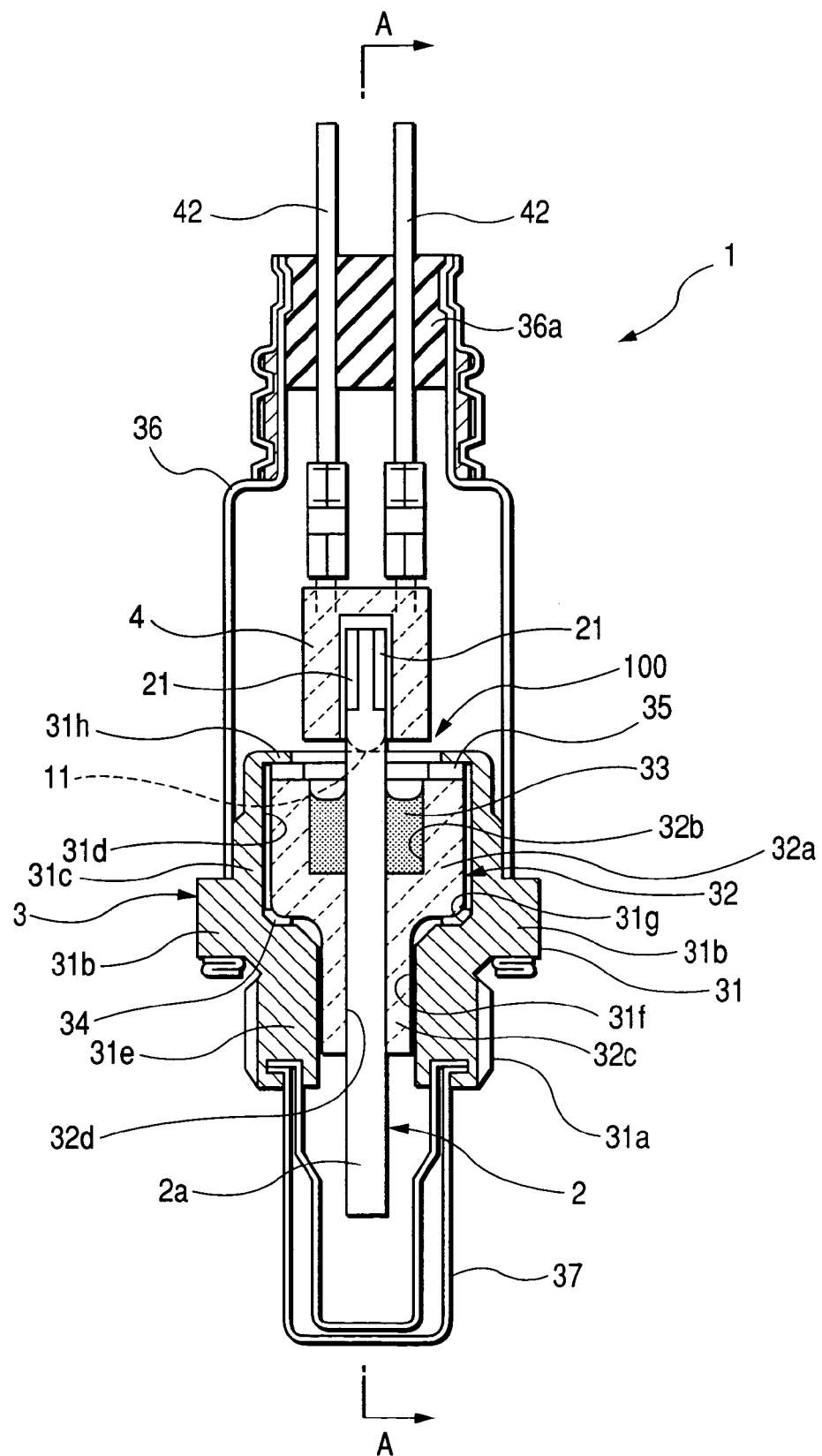
FIG. 1 is a longitudinal sectional view of a gas sensor of a first embodiment according to the present invention.

Now, gas sensors of various embodiments according to the present invention are described below in detail with reference to the accompanying drawings. However, the present invention is construed not to be limited to such embodiments described below and technical concepts of the present invention may be implemented in combination with other known technologies or the other technology having functions equivalent to such known technologies.

In the following description, like reference characters designate like or corresponding parts throughout the several views.

First Embodiment

A gas sensor of a first embodiment according to the present invention is described below in detail with reference to FIGS. 1 to 6.

Figure 2:
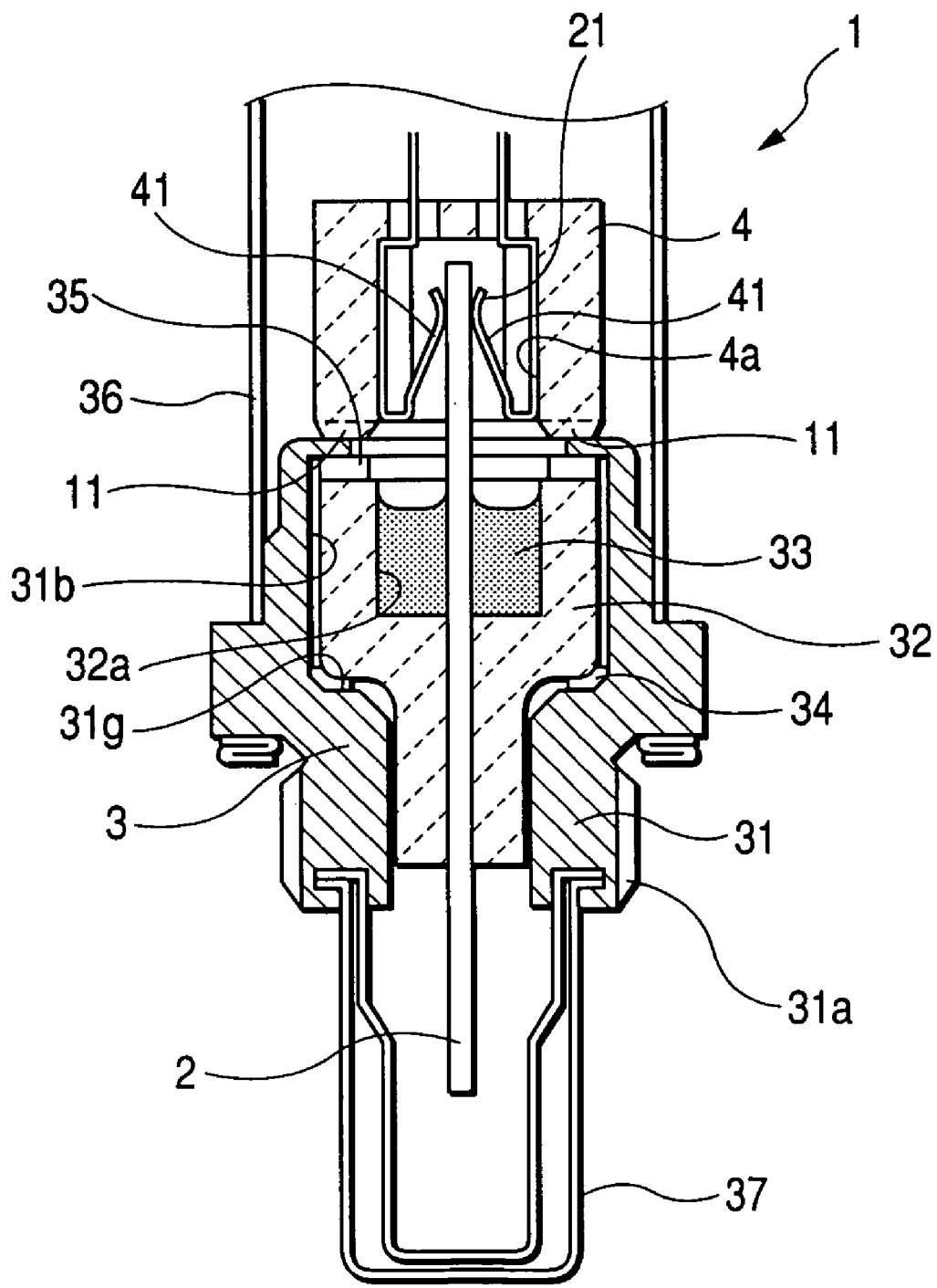
FIG. 2 is a partial cross sectional view of the gas sensor, taken on line A-A of FIG. 1, of the first embodiment shown therein.

As shown in FIGS. 1 and 2, a gas sensor 1 of the present embodiment comprises a sensor element 2, formed in rectangular shape in cross section, which has a detecting portion 2a for detecting a concentration of specified gas contained in gas (hereinafter referred to as measuring gas) to be measured and a base end portion 2b, an element holder body 3 for inserting and holding the sensor element 2, and an atmosphere-side insulator 4 placed in a position to cover a base portion of the sensor element 2 in an area closer to a base end of the element holder body 3.

The element holder body 3 comprises a housing 31, formed with a threaded portion 31a available to be screwed into a flow passage area of measuring gas to allow the sensor element 2 to detect measuring gas, and an insulation member, that is, an element-side insulator 32 fixedly mounted inside the housing 31. The sensor element 2, held inside the housing 31, is inserted through and retained with the element-side insulator 32.

Figure 3:
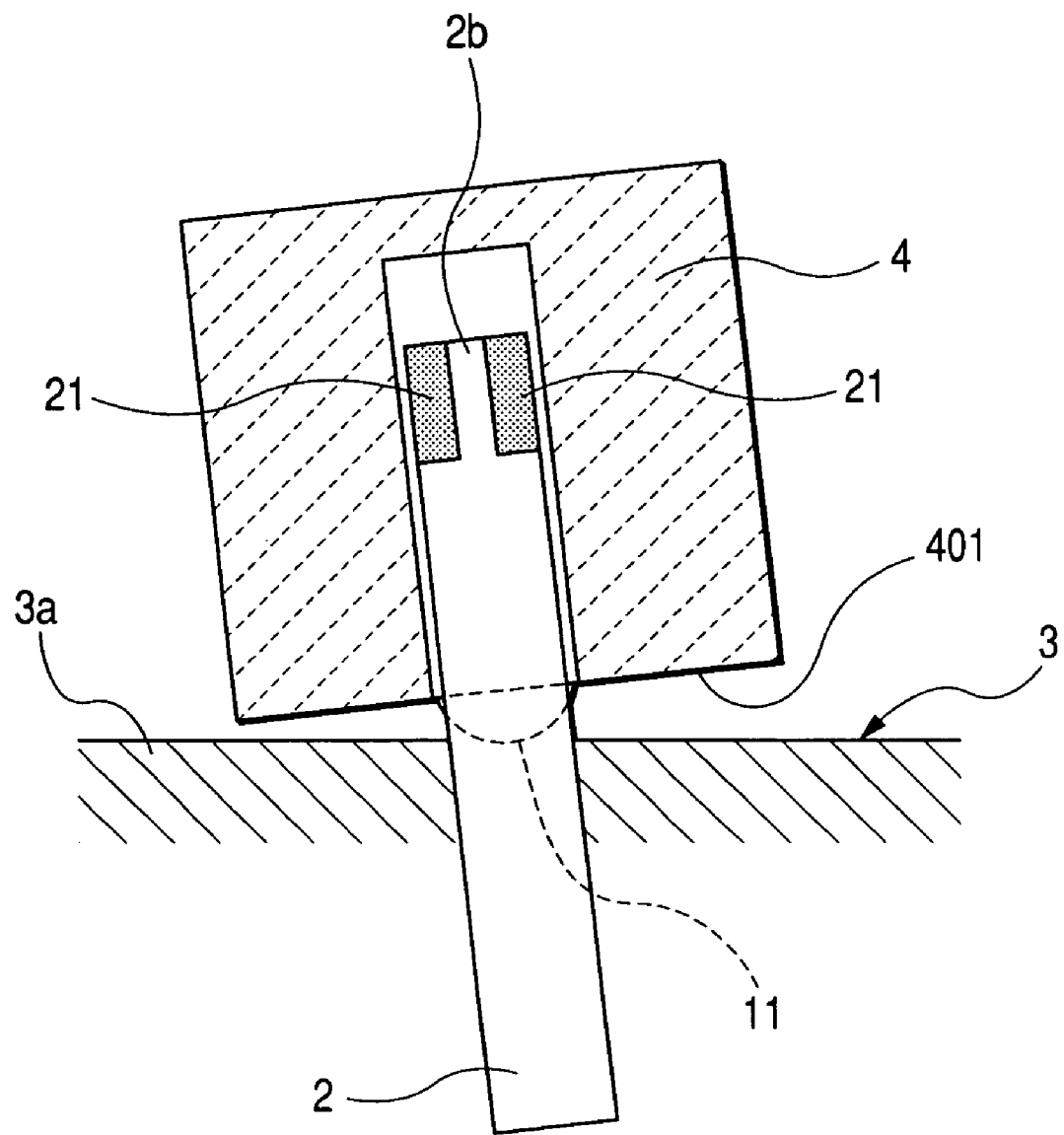
FIG. 3 is an illustrative view showing a placement condition of a sensor element with respect to an atmosphere-side insulator forming the gas sensor shown in FIG. 1.

As best shown in FIG. 3, the sensor element 2 has the base end portion 2b, that is, an upper distal end portion, which is formed with a pair of electrode terminals 21, 21 formed at spaced positions with a given distance.

Figure 4:
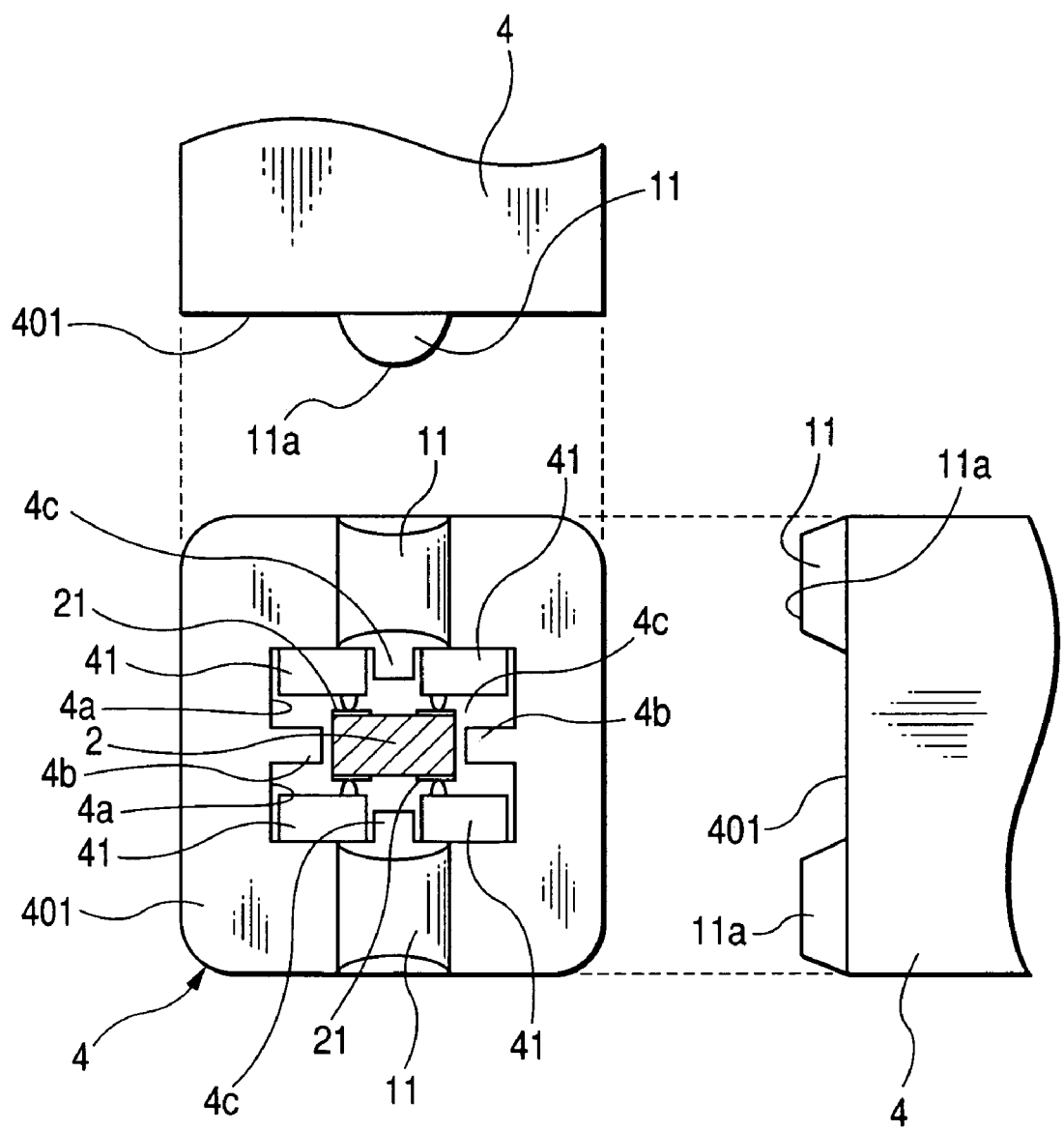
FIG. 4 is a plan view, associated with side views thereof, of a distal end of the atmosphere-side insulator forming the gas sensor shown in FIG. 1.

As shown in FIGS. 2 and 4, the atmosphere-side insulator 4, formed in square shape in cross section, has a pair of rectangular openings 4a, 4a and inwardly extending positioning protrusions 4b, 4b, 4c, 4c. The positioning protrusions 4b, 4b are placed between the rectangular openings 4a, 4a in face-to-face relationship with opposing surfaces of the sensor element 2. The positioning protrusions 4a, 4a formed in the rectangular openings 4a, 4a, respectively, at central positions on longitudinal sides thereof. Two spring terminals 41, 41 of one pair are disposed in the rectangular opening 4a in a given spaced relationship and positioned in fixed places with the positioning protrusion 4c. Likewise, two spring terminals 41, 41 of another pair are disposed in the rectangular opening 4b in a given spaced relationship and positioned in fixed places with the positioning protrusion 4c. As shown in FIG. 3, also, the atmosphere-side insulator 4 is located on a base end 3a of the element holder body 3 to allow the sensor element 2 to be matched to an axial direction.

As best shown in FIGS. 3 and 4, the gas sensor 1 further includes a tilting device 100 as will be described later. The atmosphere-side insulator 4 has a distal end 401 formed with a pair of outwardly extending convexed portions 11, playing a role as the tilting device 100, which are disposed on an axis aligned with centers of the positioning protrusions 4c, 4c. Each convexed portion 11 has a round surface 11a. Thus, the convexed portions 11 of the atmosphere-side insulator 4 are held in abutting engagement with the base end 3a of the element holder body 3, making it possible to swing the atmosphere-side insulator 4 with respect to the base end 3a of the element holder body 3.

Figure 6:
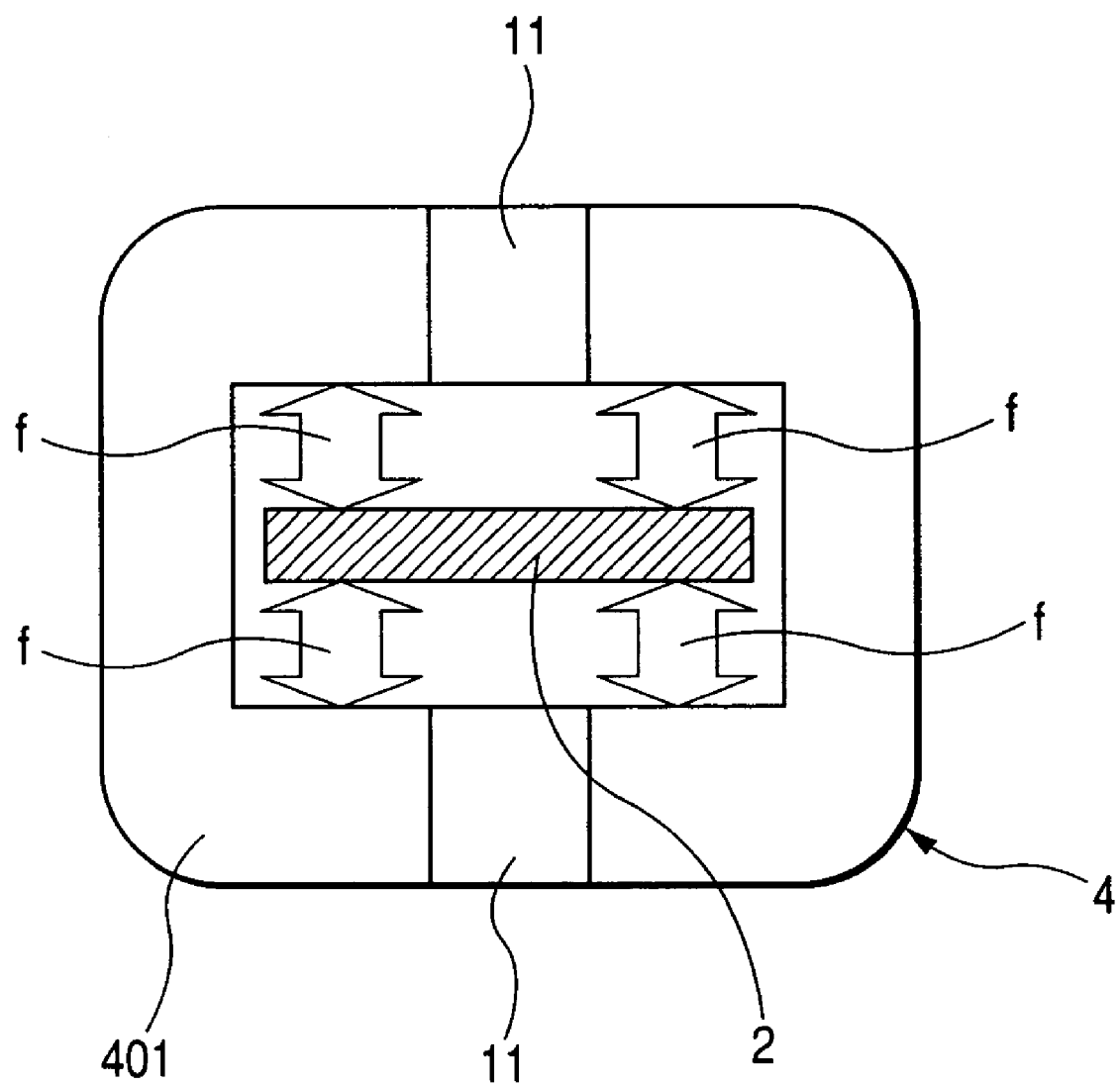
FIG. 6 is an illustrative view showing the atmosphere-side insulator having a sensor element biased by spring terminals in directions parallel to an axis of the convexed portions formed on the atmosphere-side insulator of the gas sensor shown in FIG. 1.

As shown in FIG. 6, the axis on which the convexed portions 11 are aligned to be parallel to each of orientations (designated at arrows "f") in which the spring terminals 41, 41 are biased.

More particularly, the convexed portions 11 are formed on the distal end 40a of the atmosphere-side insulator 4 at two positions along a straight line, intersecting surfaces on which the electrode terminals 21, 21 are formed, which passes across a central axis of the sensor element 2. Also, FIG. 6 is a typical view in which the spring terminals 41, 41 have biasing forces indicated by arrows "f" indicated in positions of the spring terminals 41, 41.

Figure 5A:
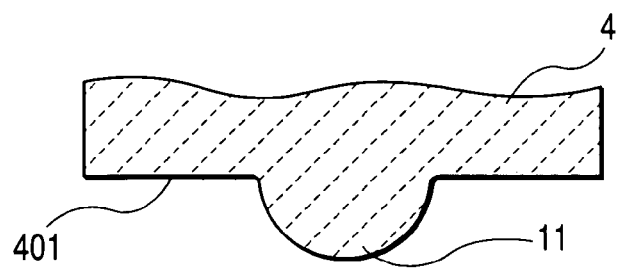
FIGS. 5A to 5E are illustrative views showing various profiles of convexed portions to be formed on the distal end of the atmosphere-side insulator of the gas sensor shown in FIG. 1.
Figure 5B:
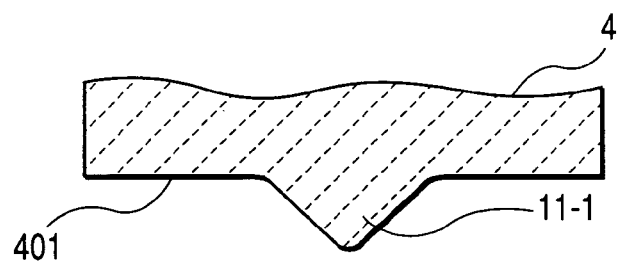
Figure 5C:
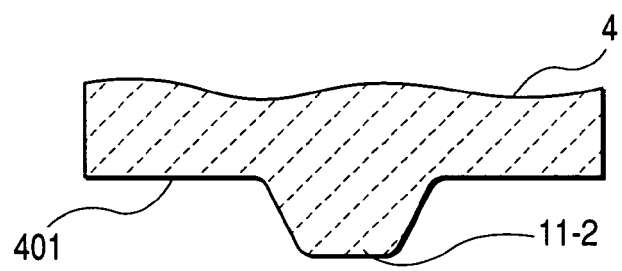
Figure 5D:
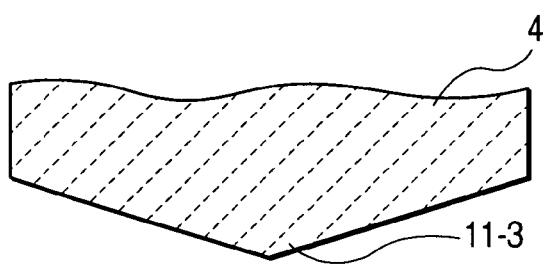
Figure 5E:
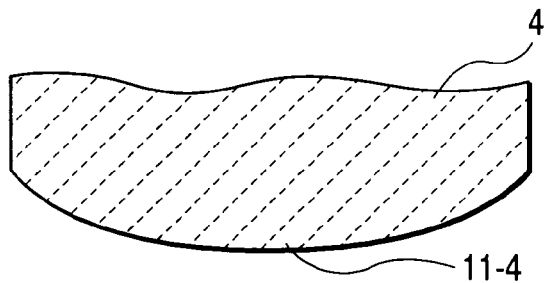

With the present embodiment, the convexed portions 11 are formed in semi circular shapes as shown in FIG. 3 and FIG. 5A. In one alternative, a convexed portion may take a substantially triangular shaped protrusion 11-1 as shown in FIG. 5B. In another alternative, a convexed portion may take a substantially trapezoid protrusion 11-2 as shown in FIG. 5C. In still another alternative, a convexed portion may take a substantially triangular profile 11-3 formed on an overall area of the distal end of the atmosphere-side insulator 4, as shown in FIG. 5D, or a substantially circular shape 11-4 formed on an overall area of the distal end of the atmosphere-side insulator 4 as shown in FIG. 5E.

Also, the convexed portion protrudes from the distal end 401 of the atmosphere-side insulator 4 by a height ranging from 0.3 to 3.0 mm.

The atmosphere-side insulator 4 is made of ceramic such as, for instance, alumina ($Al_2O_3$) or steatite ($MgO.SiO_2$) or the like.

The sensor element 2, composed of a stack type element that is structured with stacked ceramic plates each made of alumina ($Al_2O_3$) and zirconium ($ZrO_2$) or the like, that takes the form of a unitary structure including a sensor cell for detecting a concentration (such as a concentration of oxygen or a concentration of nitrogen oxide substances in exhaust gas of, for instance, an internal combustion engine), and a heater for regulating a temperature of the sensor cell, both of which are not shown.

The two electrode terminals 21 are formed on one side of the sensor element 2, whose other side is formed with the other two electrode terminals 21 are formed, with the sensor element carrying thereon a total of four terminal electrodes 21. Among these, the two electrode terminals 21 are electrically connected to the sensor cell with the other two electrodes being electrically connected to the heater.

Turning back to FIGS. 1 and 2, the element-side insulator 32 includes a cylindrical body 32a, formed with a cylindrical cavity 32b, and a cylindrical protrusion 32c formed with an axially extending inner bore 32d. The housing 31 includes a holder body member 31b having first cylindrical extension 31c, formed with a first inner bore 31d, and a second cylindrical extension 31e formed with a second inner bore 31f smaller in diameter than the first inner bore 31d. The housing 31 has an annular shoulder 31g formed between the first and second inner bores 31d, 31f.

With such a structure, the sensor element 2 is inserted through the axially extending inner bore 32d of the element-side insulator 32 and the inner cavity 32b is filled with glass sealant 33 with which the sensor element 2 is sealed in a fixed place. Moreover, the element-side insulator 32 is received in the housing 31 such that the first cylindrical member is disposed in the first cylindrical inner bore 31d of the first cylindrical extension 31c and the cylindrical protrusion 32c extends through the second inner bore 31f of the second cylindrical extension of the housing 31 with a bottom wall of cylindrical body 32a resting on the annular shoulder 31g of the holder body member 31b forming the housing 31. The first cylindrical extension 31c of the housing 31 has a distal end formed with a caulked portion 31h that extends in a radially inward direction to retain the element-side insulator 32 in a fixed place. A ring shaped disc spring 35 is interposed between and fixedly secured with the caulked portion 31h of the housing 31 and an extreme end of the cylindrical body 32a of the element-side insulator 32.

As shown in FIGS. 2 and 4, further, the four spring terminals 41, 41, placed inside the atmosphere-side insulator 4 are held in pressured contact with the relevant electrode terminals 21 so as to sandwich the base end portion 2b of the sensor element 2. In addition, the spring terminals 41, 41 are electrically connected to lead wires 42, respectively.

Further, as shown in FIGS. 1 and 2, the first cylindrical extension 31c, that if, the base portion of the housing 31 carries and fixedly supported thereon an atmosphere-side cover 36 into which a grommet 36a is fitted to support wire leads 42, 42 so as to hermetically seal the atmosphere-side insulator 4 and the sensor element 2. Moreover, the second cylindrical extension 31e, that is, a distal end of the housing 31 carries thereon a protection cover 37 for protecting the detecting portion 20a of the sensor element 2 from damage.

Now, the operation of the gas sensor 1 of the present embodiment is described below.

With the gas sensor 1, the atmosphere-side insulator 4 is mounted onto and fixedly secured to the base end of the element holder body 3. That is, as shown in FIG. 3, the atmosphere-side insulator 4 is located not based on the element holder body 3 but based on the sensor element 2. With such an arrangement, even if the sensor element 2 is inclined with respect to the element holder body 3, the atmosphere-side insulator 4 is arranged in line with the sensor element 2. Therefore, the spring terminals 41, 41 can be held in ensured electrical contact with the electrode terminals 21 without causing any misalignment between the spring terminals 41, 41 and the electrode terminals 21 of the sensor element 2.

Further, due to the provision of the convexed portions 11 formed on the distal end 401 of the atmosphere-side insulator 4, the atmosphere-side insulator 4 is held in abutting engagement with the element holder body 3 by means of the convexed portions 11. Therefore, the atmosphere-side insulator 4 is supported on the element holder body 3 with the convexed portions 11 in a stabilized arrangement. In addition, since the atmosphere-side insulator 4 is held in abutting engagement with the element holder body 3 by means of the convexed portions 11, the atmosphere-side insulator 4 can rest on the element holder body 3 at freely variable angles. This results in consequence for the atmosphere-side insulator 4 to be inclined depending on a degree of inclination of the sensor element 2.

Moreover, since the convexed portions 11 are formed on the distal end 401 of the atmosphere-side insulator 4 along the straight line parallel to the biasing directions of the spring terminals 41, 41, the atmosphere-side insulator 4 can be tilted in a direction intersecting the biasing directions of the spring terminals 41, 41, that is, in accordance with tilted angles of the electrode terminals 21 of the sensor element 2. This results in capability of ensuring adequate electrical conductance between the spring terminals 41, 41 and the electrode terminals 21.

As set forth above, with the present embodiment, a gas sensor can be provided with a structure that can ensure adequate electrical conductance between electrode terminals of a sensor element and associated spring terminals while enabling an atmosphere-side insulator to be placed on an element holder body in a stable fashion.

Second Embodiment

Next, a gas sensor 1A of a second embodiment according to the present invention is described below with reference to FIGS. 7 and 8. The gas sensor of the second embodiment is similar in structure to the gas sensor of the first embodiment except for several features and description is made with a focus on such features to omit redundant description.

Figure 7:
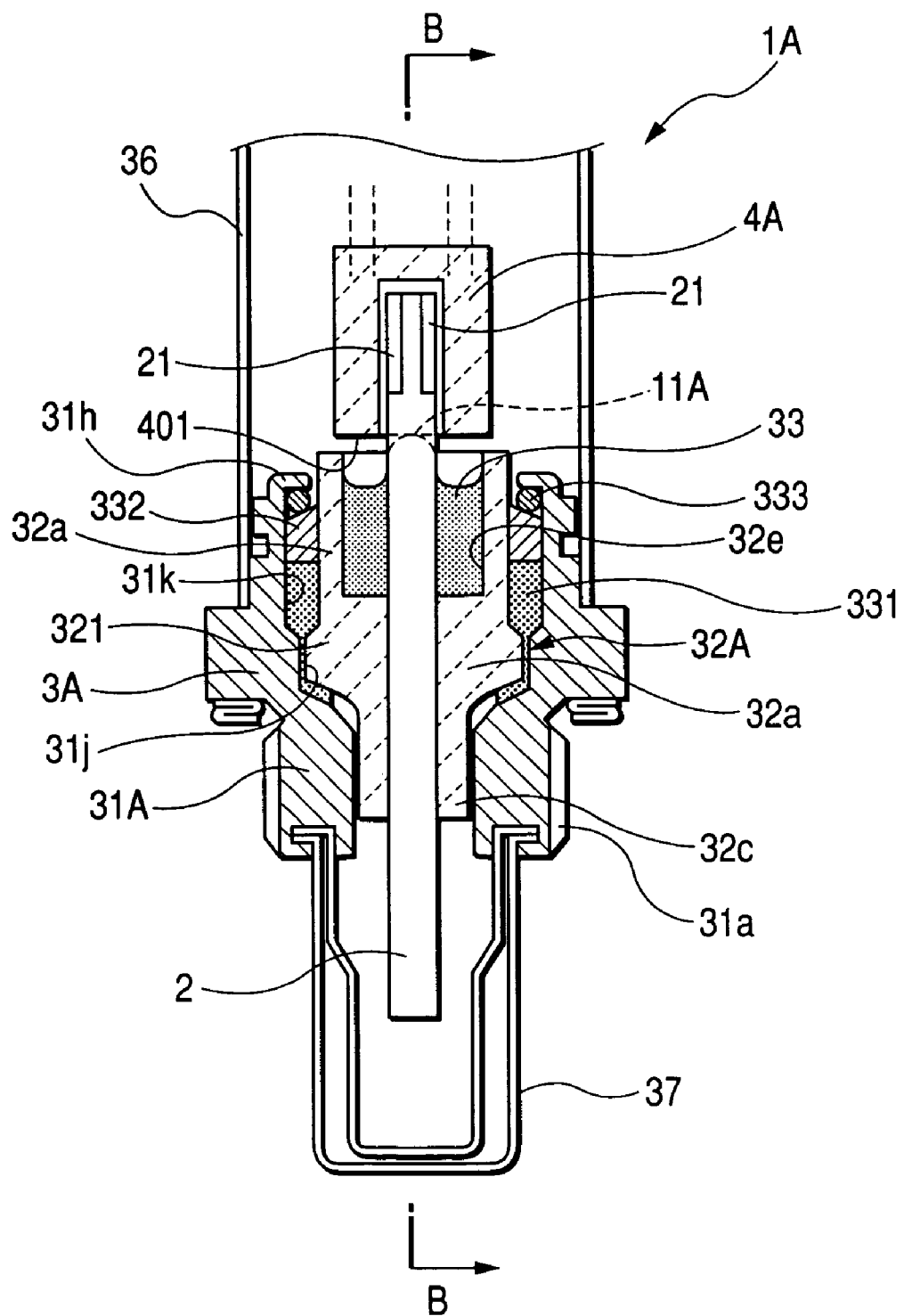
FIG. 7 is a longitudinal sectional view of a gas sensor of a second embodiment according to the present invention.
Figure 8:
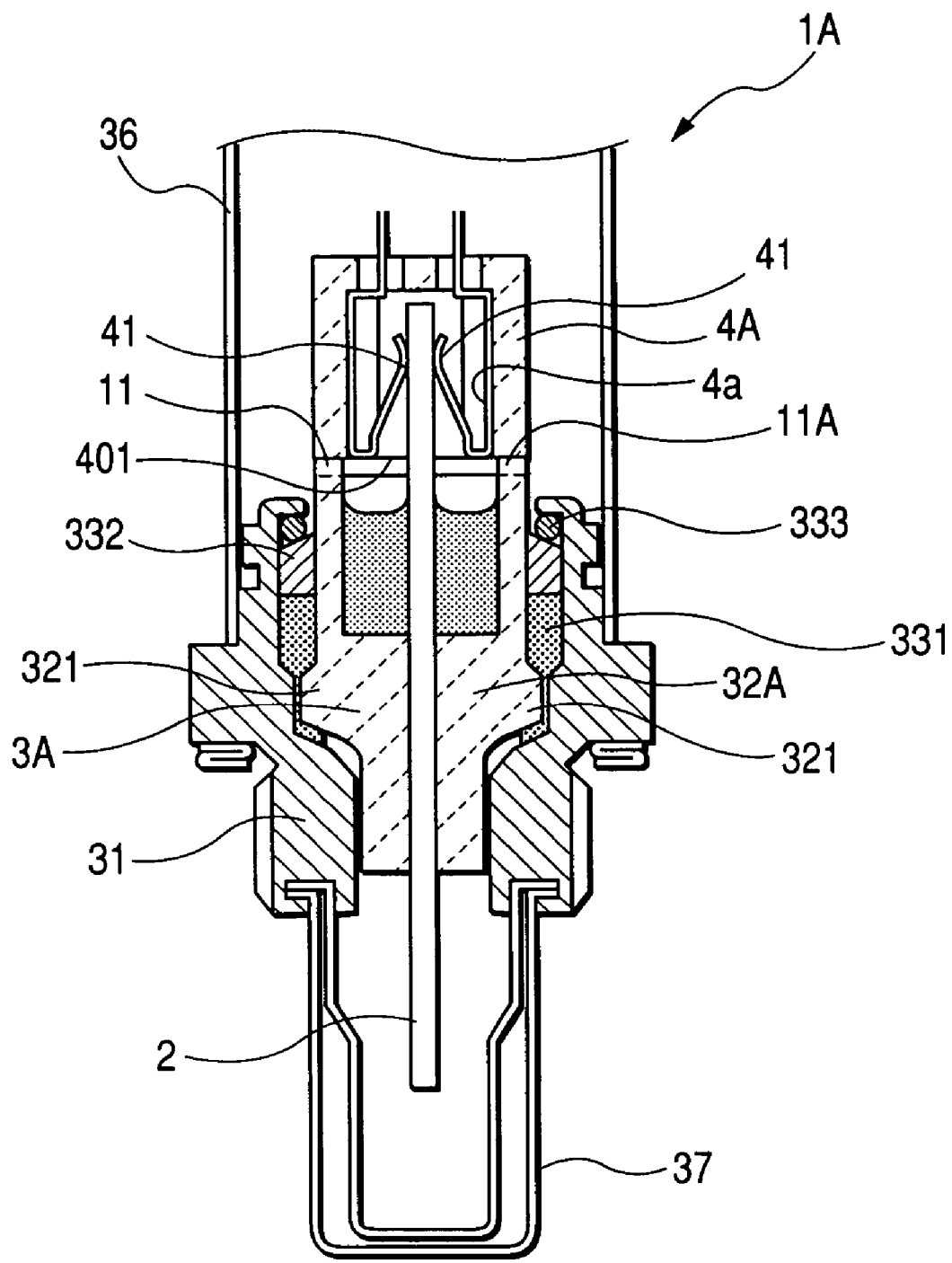
FIG. 8 is a cross sectional view taken on line B-B of FIG. 7.

FIG. 7 is a cross-sectional view of the gas sensor 1A of the second embodiment and FIG. 8 is a cross-sectional view of the gas sensor 1A, with the second embodiment representing a structure in which convexed portions 11A are formed on a base end of an element holder 3A.

With the gas sensor 1A of the second embodiment, an element holder insulator 32A, forming the element holder 3, has a cylindrical body 32a whose base end protrudes beyond a base end, that is, the caulked portion 31h of the housing 31A. Further, the cylindrical body 32a has a large diameter portion 321, formed between the first and second cylindrical portions 32a and 32c, which is received in an inner bore 31j of the element holder 3A forming the housing 3A. Defined between an inner bore 31k of the housing 31A and an outer periphery of the first cylindrical body 32a is an annular space in which a sealant 331, an insulation member 332 and a metallic ring 333 are sequentially disposed in stacked condition upon which a base end of the housing 31A is caulked to form the caulked portion 31h to hold these component parts in fixed places. This allows a clearance between the element-side insulator 32A and the housing 31A to be tightly sealed such that these component elements are fixedly secured to each other.

With the structure set forth above, the convexed portions 11A are formed on an upper end wall of the cylindrical body 32a forming the element-side insulator 32A forming the element holder 3A. An atmosphere-side insulator 4 has a distal end 401 that is held in abutting engagement with the convexed portions 11A.

Even with the gas sensor 1A of the present embodiment, the convexed portions 11A can be formed on the distal end of the cylindrical body 32a of the element-side insulator 32A in an easy and reliable manner. Also, the atmosphere-side insulator 4 can be supported on the element holder 3A for tilting capability in a stable manner. In addition, the gas sensor 1A of the second embodiment operates in the same manner as the gas sensor 1 of the first embodiment.

Third Embodiment

Next, a gas sensor 1B of a third embodiment according to the present invention is described below with reference to FIGS. 9 to 11. The gas sensor 1B of the third embodiment is similar in structure to the gas sensor 1 of the first embodiment except for several features and description is made with a focus on such features to omit redundant description.

Figure 9:
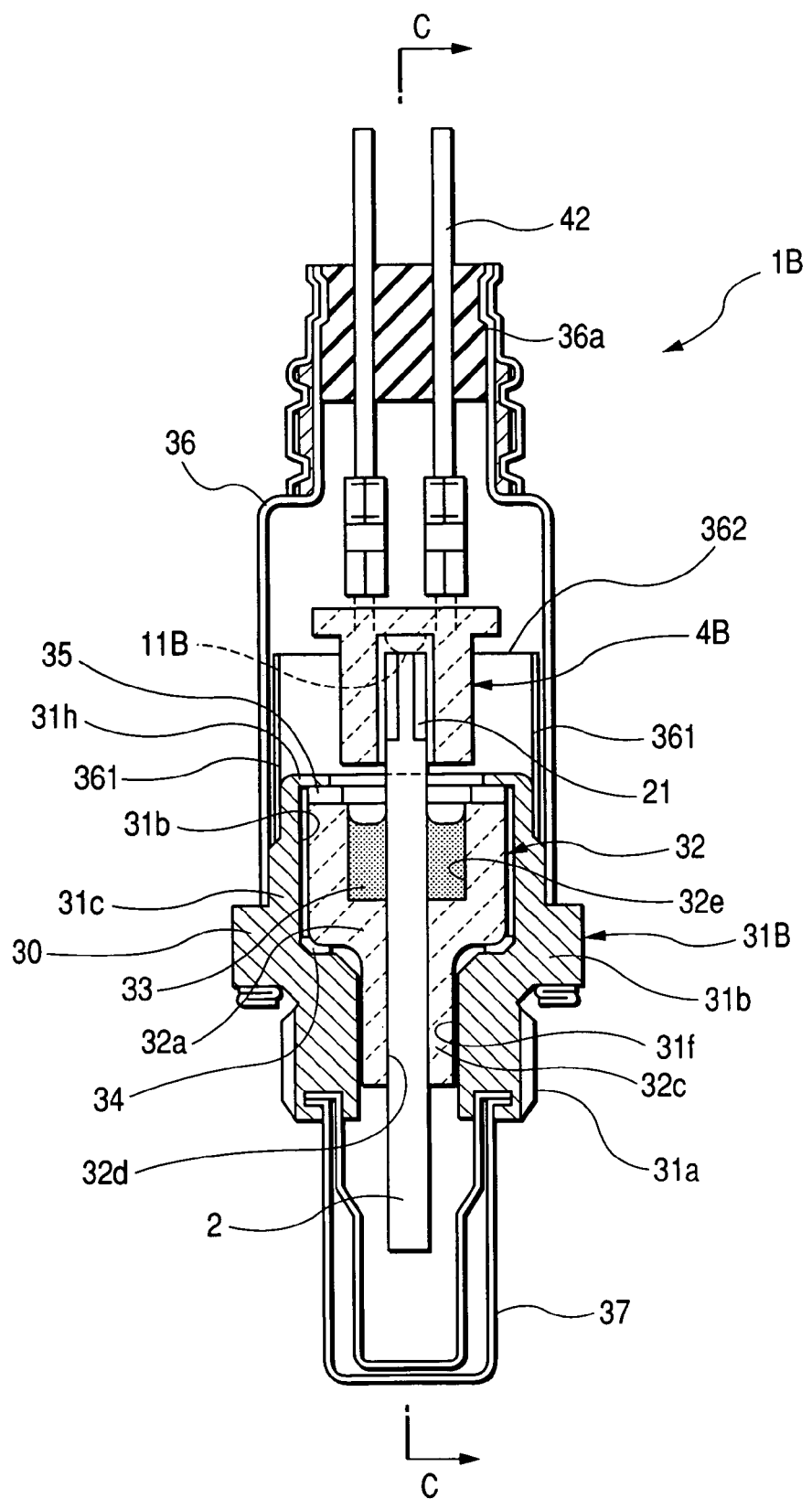
FIG. 9 is a longitudinal sectional view of a gas sensor of a third embodiment according to the present invention.
Figure 10:
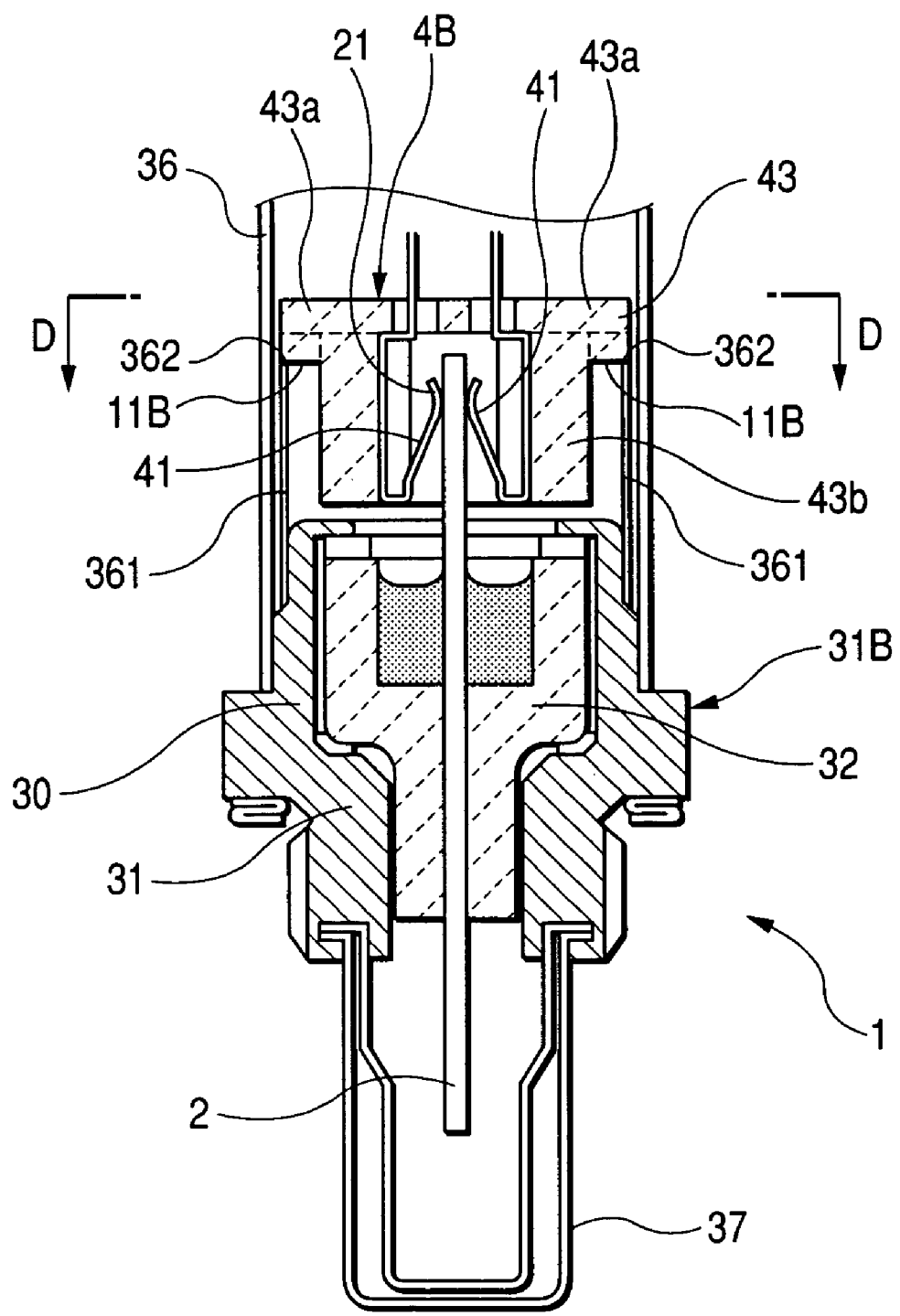
FIG. 10 is a cross sectional view taken on line C-C of FIG. 9.

FIG. 9 is a cross-sectional view of the gas sensor 1B of the third embodiment and FIG. 10 is a cross-sectional view, taken on line C-C of FIG. 9, of the gas sensor 1B, with the third embodiment representing a structure in which an atmosphere-side 4B and the sensor element 2. FIG. 11 is a cross-sectional view of the gas sensor 1B taken on line D-D of FIG. 10.

With the third embodiment, the gas sensor 1B includes an inner protection cylinder 361, coaxially disposed in the base end of the atmosphere-side cover 36 and supported with the base end of a housing 31B, which has one base end fixedly supported with an outer periphery of the first cylindrical extension 31c and the other base end portion 362 with which the atmosphere-side 4B is supported.

Figure 11:
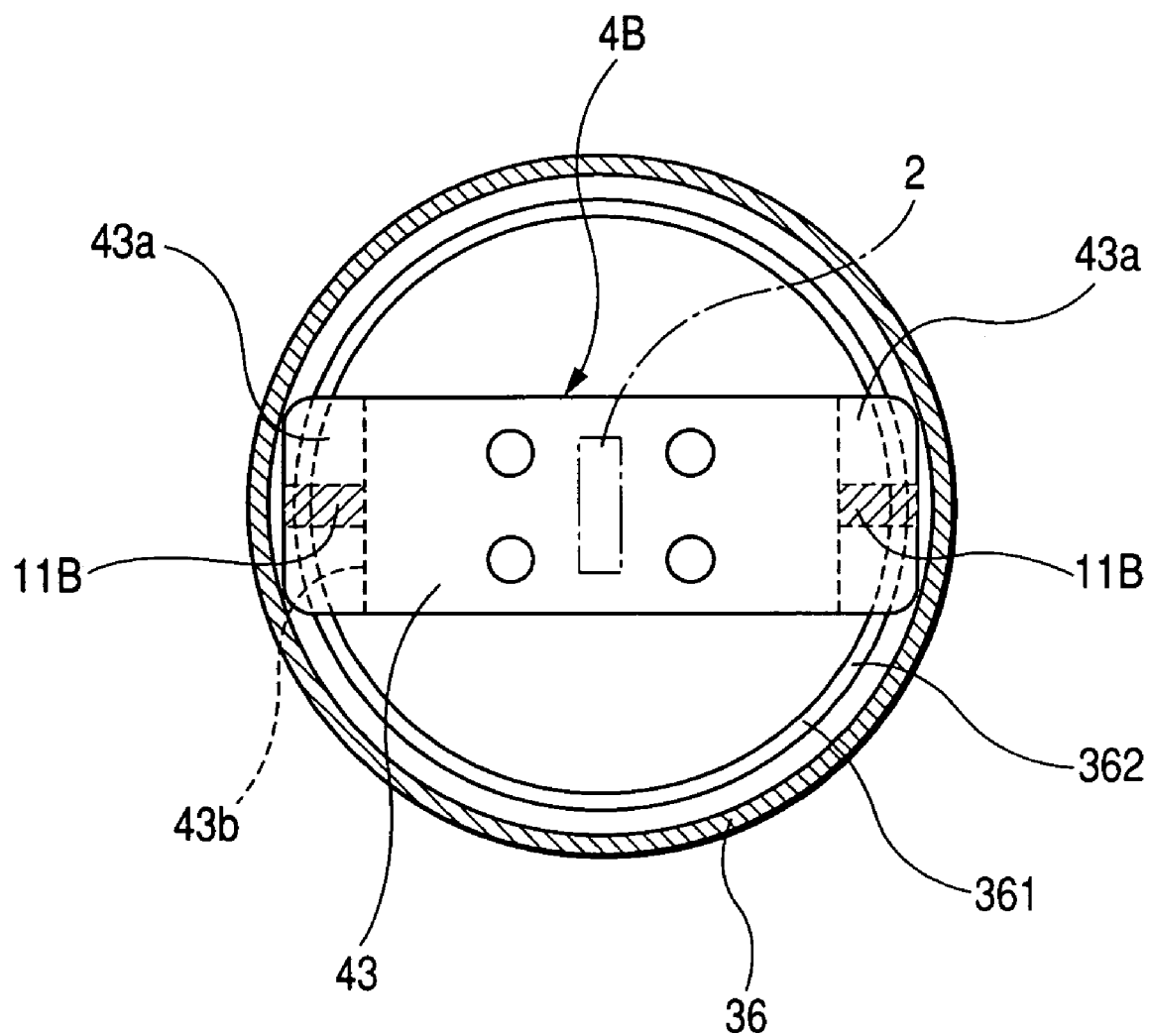
FIG. 11 is a cross sectional view taken on line D-D of FIG. 10.

As best shown in FIGS. 10 and 11, the atmosphere-side insulator 4B includes a rectangular base portion 43, disposed in the atmosphere-side cover 36 and having both ends formed with radial protrusions 43a, 43a, and a receptor portion 43b extending downward from the base portion 43. The radial protrusions 43a, 43a of the base portion 43 have bottom wall formed with downwardly facing convexed portions 11B, 11B that are held in abutting engagement with the base end portion 362 of the inner protection cylinder 361.

Even with the present embodiment, the gas sensor 1B can ensure electrical conductance between the spring terminals 41 and the electrode terminals 21 of the sensor element 2 in a highly reliable manner. In addition, the atmosphere-side insulator 4B can be supported on the element holder 30 in a stabilized manner. Also, the gas sensor 1B of the present embodiment operates in the same manner as that of the gas sensor 1 of the first embodiment.

Figure 12:
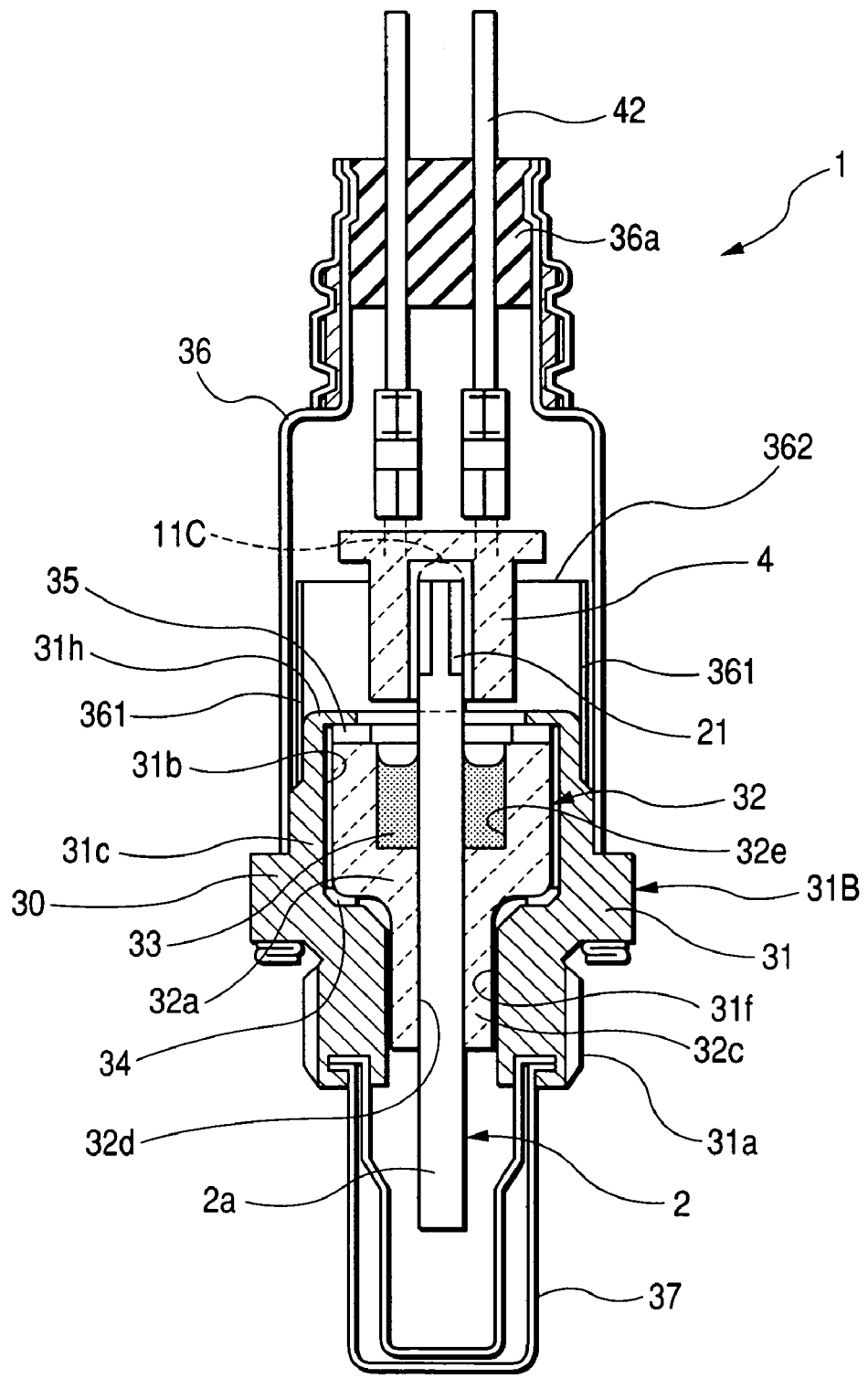
FIG. 12 is a longitudinal sectional view of a gas sensor of a modified form of the third embodiment shown in FIGS. 9 to 11.

Also, the gas sensor 1B of the third embodiment may be modified such that in place of providing the convexed portions on the radial extensions 43a, 43a of the atmosphere-side insulator 4B, the inner protection cylinder 361 has the base end portion 362 formed with convexed portions 11C on which bottom walls of the radial extensions 43a, 43a rests as shown in FIG. 12.

Fourth Embodiment

Next, a gas sensor 1C of a fourth embodiment according to the present invention is described below with reference to FIGS. 13A and 13B. The gas sensor 1C of the fourth embodiment is similar in structure to the gas sensor 1 of the first embodiment except for several features and description is made with a focus on such features to omit redundant description.

Figure 13A:
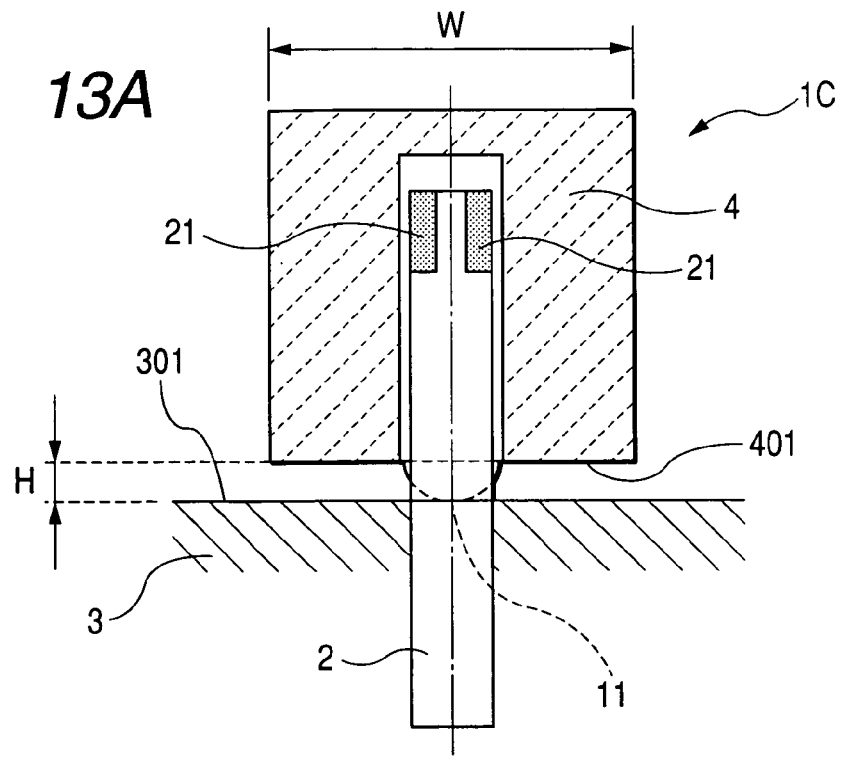
FIG. 13A is an illustrative view of a gas sensor of a fourth embodiment according to the present invention and showing a placement condition between a sensor element and an atmosphere-side insulator with an element holder body having a greater width than that of the atmosphere-side insulator.
Figure 13B:
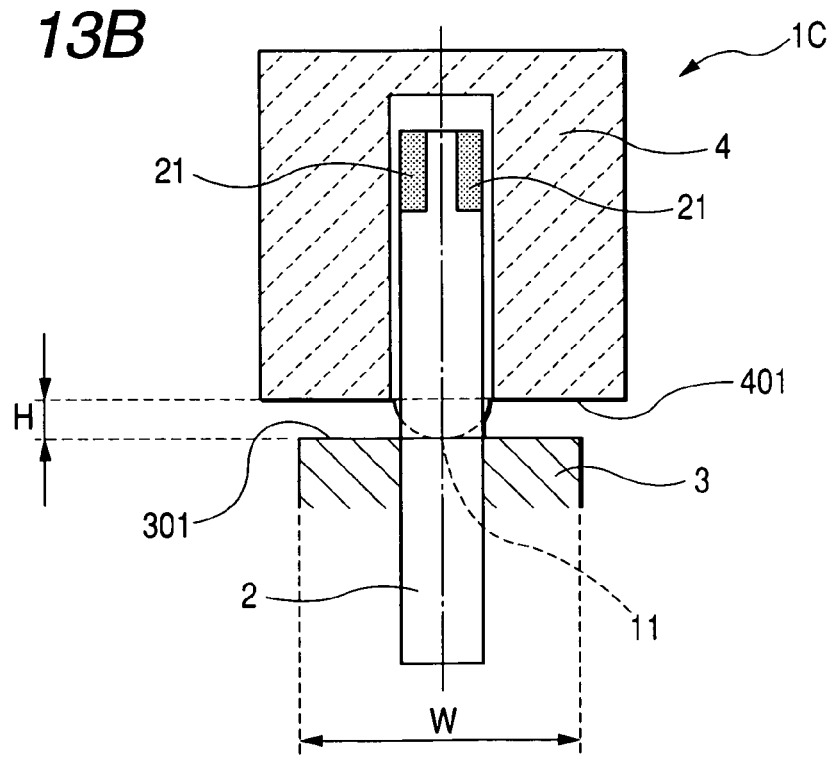
FIG. 13B is an illustrative view of a gas sensor of the fourth embodiment according to the present invention and showing another placement condition between the sensor element and the atmosphere-side insulator with the element holder body having a smaller width than that of the atmosphere-side insulator.
Figure 15:
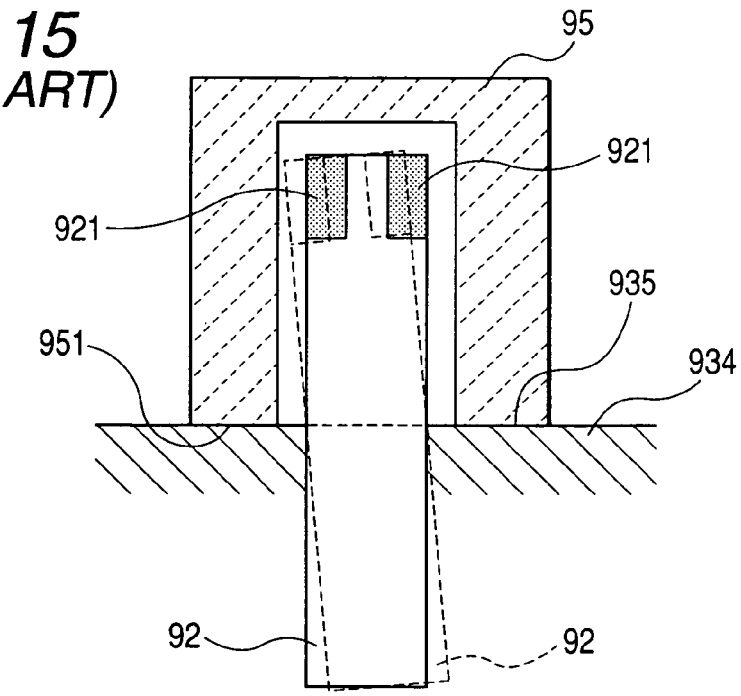
FIG. 15 is an illustrative view showing the gas sensor of the related art under a status where a sensor element is placed in a tilted condition.
Figure 16:
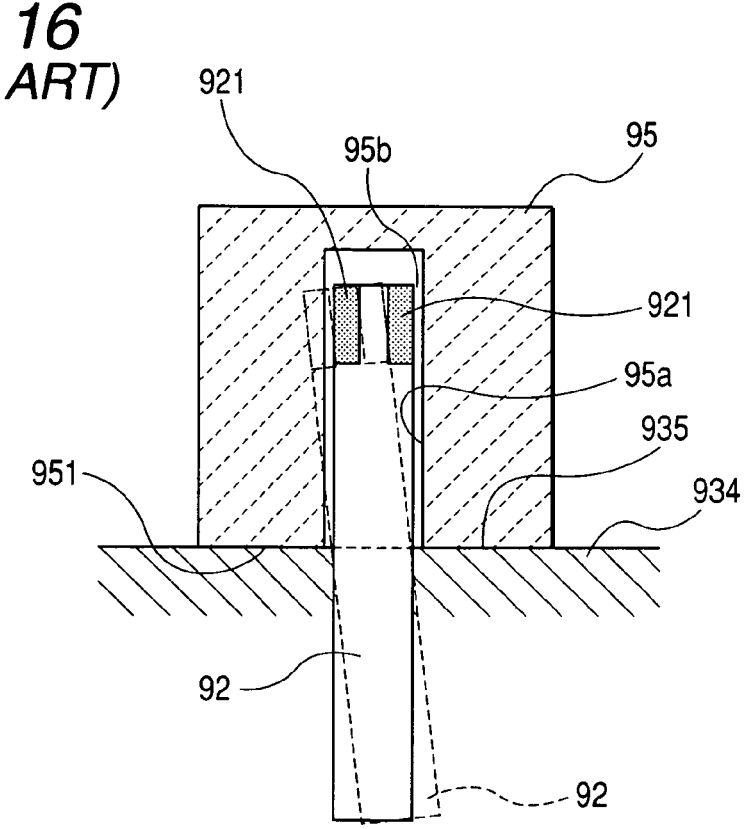
FIG. 16 is an illustrative view showing the gas sensor of the related art with a minimized space kept between a sensor element and an atmosphere-side insulator.
Figure 17:
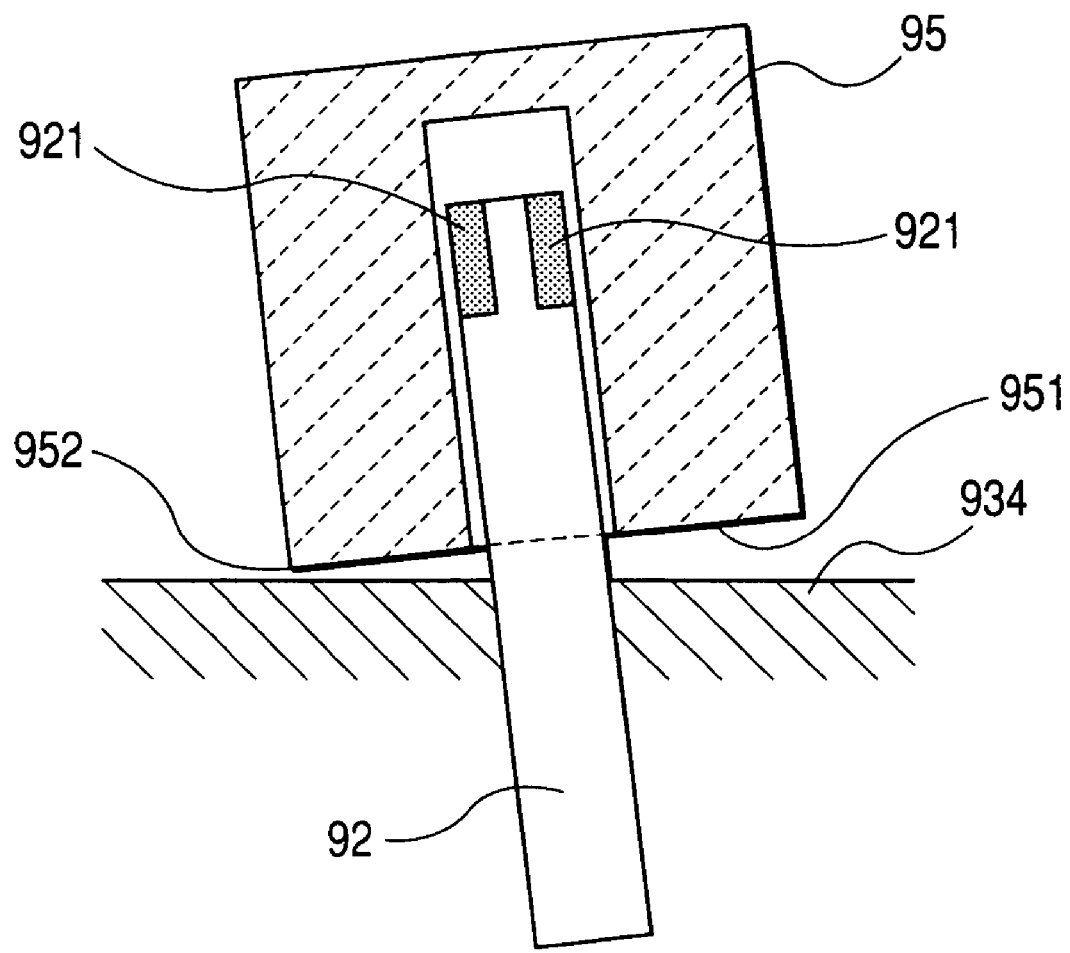
FIG. 17 is an illustrative view showing the gas sensor of the related art with the atmosphere-side insulator being placed with respect to the sensor element.

FIG. 13A is an enlarged cross-sectional view showing an essential part of the gas sensor 1C of the fourth embodiment and FIG. 13B is a cross-sectional view of the gas sensor 1C of the fourth embodiment.

With the fourth embodiment, the gas sensor 1C has a specified relationship among a width W1 of a distal end 401 of an atmosphere-side insulator 4C, a width W of a base end 301 of an element holder body 3 and a protruding length H of the convexed portions 11.

With the present embodiment, the convexed portions 11 are formed on the distal end 401 of the atmosphere-side insulator 4C with the protruding length H from the distal end 401 of the atmosphere-side insulator 4C.

With the gas sensor 1C shown in FIG. 13A, the width W of the base end 301 of the element holder body 3 is set to be greater than the width W of the distal end 401 of the atmosphere-side insulator 4 in a direction intersecting the biasing directions of the spring terminals 41 (see FIG. 6). In such a case, suppose that the width of the distal end 401 of the atmosphere-side insulator 4 in the direction intersecting the biasing directions of the spring terminals 41 is assigned to be W, the relationship is established as H/W>0.1.

Further, with the gas sensor 1C shown in FIG. 13B, the distal end 401 of the atmosphere-side insulator 4C has the width greater than a width W2 of the base end 301 of an element holder body 3. In such a case, suppose that the width of the base end 301 of the element holder body 3 in a direction intersecting the biasing directions of the spring terminals 41 is assigned to be W, the relationship is established as H/W>0.1.

With such arrangements mentioned above, it becomes possible to prevent the sensor element 2 from being damaged. That is, the sensor element 2 has a probability to tilt at an angle of approximately 1° with respect to the element holder body 3. Even with such a probability, if the relationship is established as H/W>0.1, then, the atmosphere-side insulator 4 and the element holder body 3 can be prevented from the occurrence of contact with each other at a position except for the convexed portions 11. That is, the atmosphere-side insulator 4 and the element holder body 3 can be brought into abutting engagement with each other by means of the convexed portions 11. This leads to a consequence of preventing the atmosphere-side insulator 4 from floating from the element holder body 3. This suppresses impact or load from acting on the sensor element 2 from the atmosphere-side insulator 4. This results in capability of preventing the sensor element 1 from being damaged.

Also, the gas sensor 1C of the present embodiment operates in the same manner as the gas sensor 1 of the first embodiment.

Moreover, even a structure having the convexed portions 11 formed o the base portion 301 of the element holder body 3 has the same effects as those set forth above.

Also, in actual practice, the width of the atmosphere-side insulator 4 and the width of the base end of the element holder body may preferably have the relationship expressed as H/W>0.2 in anticipation of the sensor element 2 tilting at an angle of approximately 5° with respect to the element holder body 3.

While the specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention, which is to be given the full breadth of the following claims and all equivalents thereof.

What is claimed is:

1. A gas sensor comprising:
an element holder body including a housing, available to be mounted on a gas flow passage for gas to be measured, and an insulation member fixedly supported in the housing;
a sensor element, fixedly supported in the insulation member, which has a base end whose opposing surfaces are formed with a plurality of electrode terminals, respectively;
an atmosphere-side insulator covering the base end of the sensor element and internally incorporating a plurality of spring terminals held in contact with the electrode terminals, respectively; and
a tilting device disposed between the atmosphere-side insulator and the element holder body and including at least one convexed portion formed on at least one of the atmosphere-side insulator and the element holder, the convexed portion having an apex portion in abutting contact with a surface of the other one of the atmosphere-side insulator and the element holder such that the atmosphere-side insulator rests on the element holder so as to be tiltable relative to an axis of the element holder at freely variable angles to be inclined depending on a degree of inclination of the sensor element.

2. The gas sensor according to claim 1, wherein:
the convexed portion is formed on a distal end of the atmosphere-side insulator along an axis parallel to a biasing direction of each of the spring terminals.

3. The gas sensor according to claim 1, wherein:
the tilting device comprises convexed portions formed on a base end of the element holder body along an axis parallel to a biasing direction of each of the spring terminals.

4. The gas sensor according to claim 1, wherein:
the element holder body comprises an atmosphere-side cover fixedly secured to a base end of the housing so as to cover the atmosphere-side insulator, and an inner protection cylinder disposed inside the atmosphere-side cover and fixedly supported with the base ed of the housing in an area outside the atmosphere-side insulator; and
the tilting device comprises a radial protrusion, radially extending from the atmosphere-side insulator in an area inside the atmosphere-side cover, which is held in abutting engagement with the inner protection cylinder to be tiltable at the given tilting angle.

5. The gas sensor according to claim 4, wherein:
the tilting mechanism comprises a convexed portion formed on the radial protrusion of the atmosphere-side insulator.

6. The gas sensor according to claim 4, wherein:
the tilting mechanism comprises a convexed portion formed on the inner protection cylinder in abutting engagement with the radial protrusion of the atmosphere-side insulator.

7. The gas sensor according to claim 1, wherein:
the tilting device comprises a convexed portion formed on one of the atmosphere-side insulator and the element holder body; and
the atmosphere-side insulator and the element holder body has the relationship expressed as H/W>0.1
where H represents a protruding length of the convexed portion from one of the atmosphere-side insulator and the element holder body and W represents a smaller width of the one of the atmosphere-side insulator and the element holder body than a width of the other one of the atmosphere-side insulator and the element holder body.

8. The gas sensor according to claim 1, wherein:
the housing includes a holder body member, a first cylindrical extension, extending in a direction toward the atmosphere-side insulator and internally holding the insulation member, and a second cylindrical extension extending from the holder body member in opposition to the first cylindrical extension;
wherein the first cylindrical extension has a radially inward portion facing the atmosphere-side insulator; and
wherein the tilting member comprises a convexed portion held in abutting engagement with the radially inward portion of the first cylindrical extension.

9. The gas sensor according to claim 1, wherein:
the insulation member comprises an element-side insulator including a cylindrical body whose base end extends from the housing of the element holder body; and
wherein the tilting device comprises a convexed portion held in abutting engagement with the atmosphere-side insulator.

* * * * *